(12) United States Patent
Butler

(10) Patent No.: US 8,151,800 B2
(45) Date of Patent: Apr. 10, 2012

(54) HYGIENIC ORAL BIB

(75) Inventor: Leroy Butler, Detroit, MI (US)

(73) Assignee: Stratus Global LLC, Ann Arbor, MI (US)

( * ) Notice: Subject to any disclaimer, the term of this patent is extended or adjusted under 35 U.S.C. 154(b) by 268 days.

(21) Appl. No.: 12/533,297

(22) Filed: Jul. 31, 2009

(65) Prior Publication Data

US 2010/0024832 A1    Feb. 4, 2010

Related U.S. Application Data

(63) Continuation-in-part of application No. 11/204,809, filed on Aug. 16, 2005, now abandoned.

(60) Provisional application No. 60/602,101, filed on Aug. 17, 2004.

(51) Int. Cl.
*A61C 5/14*    (2006.01)
*A42B 1/08*    (2006.01)

(52) U.S. Cl. .............. 128/860; 128/857; 2/424

(58) Field of Classification Search .......... 128/842, 128/844, 918, 857–862, 206.21, 846, 848; 2/2, 15, 410
See application file for complete search history.

(56) References Cited

U.S. PATENT DOCUMENTS

| | | | |
|---|---|---|---|
| 4,949,731 A | | 8/1990 | Harding |
| 4,974,605 A * | | 12/1990 | Esqueda ............ 128/857 |
| 5,016,649 A | | 5/1991 | Johnson |
| 5,320,112 A * | | 6/1994 | Bloodsaw ............ 128/842 |
| 5,441,046 A * | | 8/1995 | Starr et al. ........... 128/207.11 |
| 5,570,705 A | | 11/1996 | Burke |
| 5,582,187 A | | 12/1996 | Hussey |
| 6,572,569 B2 | | 6/2003 | Klein |
| 6,997,888 B2 | | 2/2006 | Rehrig |
| 2007/0193586 A1 * | | 8/2007 | Vaughn ............ 128/844 |

* cited by examiner

*Primary Examiner* — Patricia Bianco
*Assistant Examiner* — Tarla Patel
(74) *Attorney, Agent, or Firm* — Patent Procurement Services

(57) ABSTRACT

An oral bib includes a thin sheet protective shield portion having resistance to the passage of a sexually transmitted disease microbe therethrough. The shield portion is configured to overlie a chin and mouth region of a wearer and has opposing sides. A strap is adapted to secure said shield portion to a wearer head.

11 Claims, 5 Drawing Sheets

HYGIENIC ORAL BIB

CROSS-REFERENCE TO RELATED APPLICATIONS

This application is a continuation-in-part of U.S. patent application Ser. No. 11/204,809 filed Aug. 16, 2005 is now abandoned, which claims priority of U.S. provisional application No. 60/602,101 filed Aug. 17, 2004, the contents of which are hereby incorporated by reference.

FIELD OF THE INVENTION

The present invention in general relates to a barrier against sexually transmitted diseases and in particular to a face-mounted barrier.

BACKGROUND OF THE INVENTION

While condoms have gained general acceptance for their effectiveness in preventing the spread of sexually transmitted diseases (STDs) during intercourse, the dental dam has generally met with limited acceptance. The dental dam, originally developed as an adjunct to dental procedures, has been adapted as a barrier against the spread of STDs during oral sex. The dental dam has a thin sheet of latex which serves as a barrier between partners when placed intermediate therebetween. However, oral dams tend to become displaced from the recipient partner's anal or vaginal area during usage. Thus, there exists a need for an oral protective device against sexually transmitted diseases that is not readily displaced from between sexual partners.

SUMMARY OF THE INVENTION

An oral bib includes a thin sheet protective shield portion having resistance to the passage of a sexually transmitted disease microbe therethrough. The shield portion is configured to overlie a chin and mouth region of a wearer and has opposing sides. A strap is adapted to secure said shield portion to a wearer head.

BRIEF DESCRIPTION OF THE DRAWINGS

The present invention is further illustrated with respect to the following exemplary and non-limiting embodiments depicted in the accompanying drawings.

FIGS. 3A-3F represent alternate textural embodiments of blade portions of an inventive bib;

DETAILED DESCRIPTION OF THE INVENTION

The present invention has utility as a device for the prevention of STDs that otherwise are transmitted by oral sex. A thin elastomeric sheeting material that is resistant to transmission therethrough of microbes is fashioned to secure around the chin and mouth of a user and retained in this position with a securement encompassing the ears or head of the user.

Figure 1:
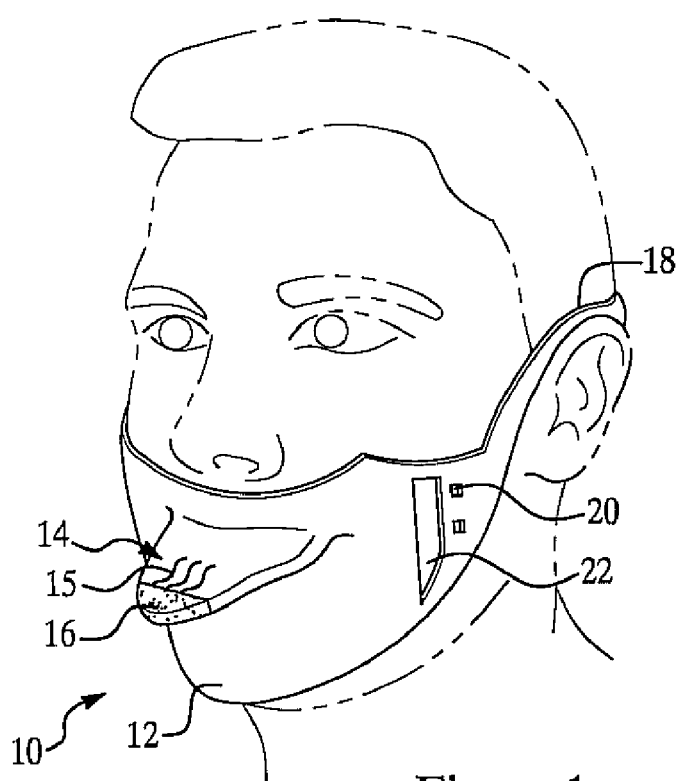
FIG. 1 is a perspective view of an inventive hygienic oral bib.
Figure 2:
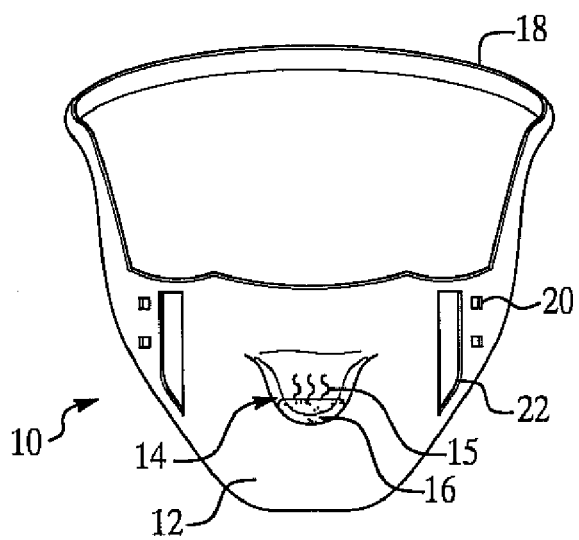
FIG. 2 is a frontal view of the inventive bib depicted in FIG. 1.
Figure 3A:
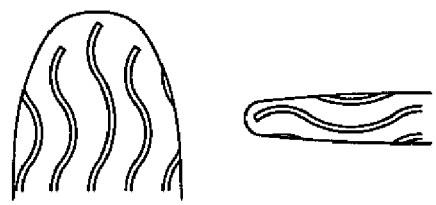
Figure 3B:
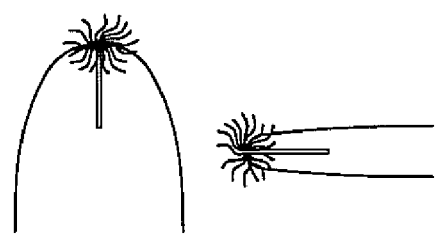
Figure 4A:
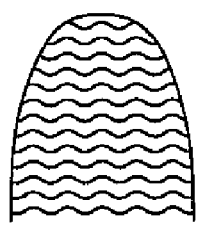
FIGS. 4A-4F are perspective views of inventive embodiments having alternate strap configurations.
Figure 4A:
Figure 4A:
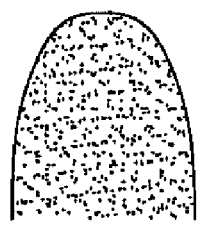
Figure 4A:
Figure 4A:
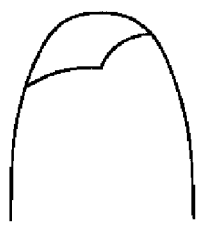
Figure 4A:
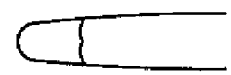
Figure 4A:
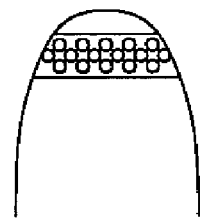
Figure 4A:
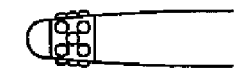
Figure 4A:
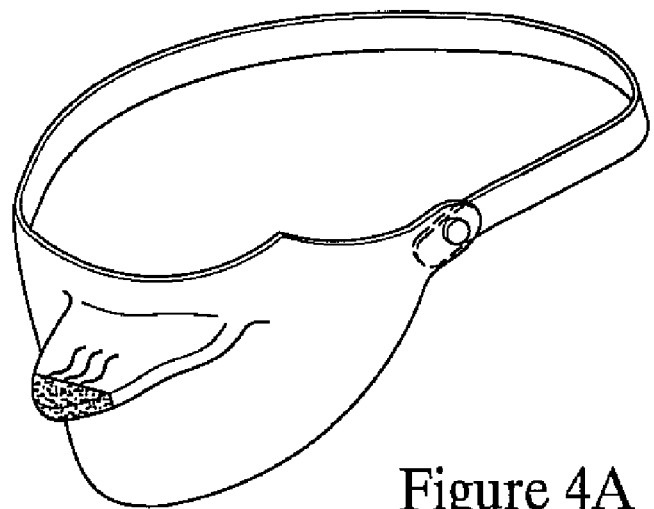
Figure 4B:
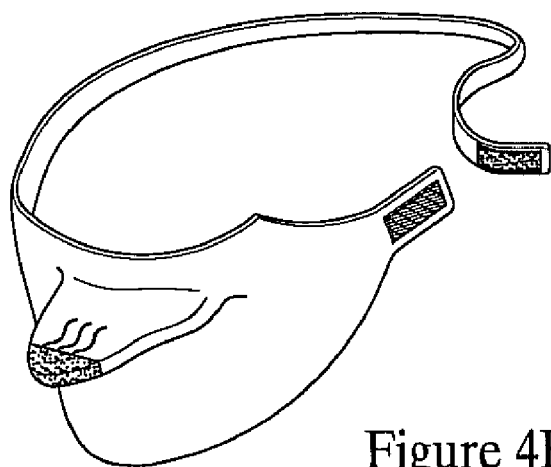
Figure 4C:
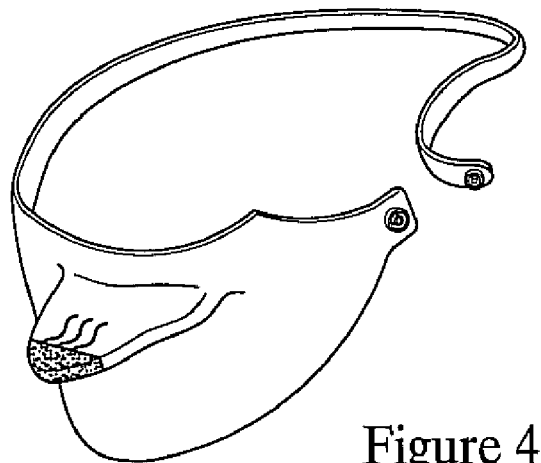
Figure 4D:
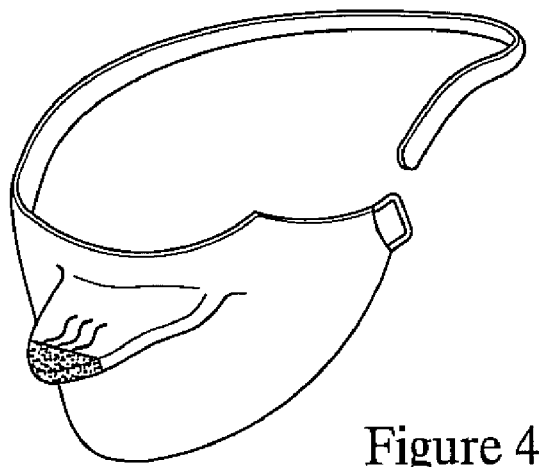
Figure 4E:
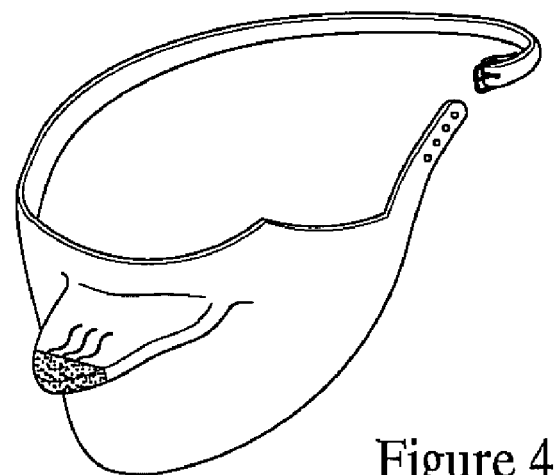
Figure 4F:
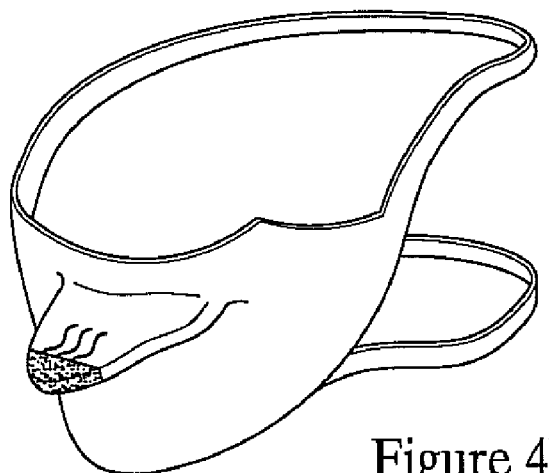

Referring now to FIGS. 1 and 2, an inventive bib is shown generally at 10. The bib 10 has a shield portion 12 encompassing the chin and mouth region of a user. Preferably, the shield portion 12 includes a tongue sheath portion 14 positioned upon placement over a wearer's face so as to overlie a user mouth. The shield portion 12 is constructed of an elastomeric sheet material resistant to the passage of STD causing organisms therethrough. As such, the shield material is preferably pore free or, if pores are present, such pores are less than about 0.2 microns. Shield portion materials illustratively include latex rubber, silicone rubber, polyalkylenes, and other materials conventional for the production of synthetic polymer condoms.

A tongue portion 14 is appreciated to be formed from a continuous sheet of material making up the shield portion or alternatively to be formed from a separate piece of material with the proviso that a hermetic seal is formed at the interface between tongue portion and shield portion. The tongue portion 14 is readily formed of the same materials as the shield portion 12, yet dissimilar materials for the tongue portion 14 and shield portion 12 are recognized to be operative herein. Methods of forming a hermetic seal between the shield and tongue portions illustratively include thermal welding, sonic welding, and contact adhesives. Optionally, the tongue portion 14 has contours 15. An illustrative group of such contours is depicted in FIGS. 3A-3F and include longitudinal waves, pilli, transverse waves, dimples, a step, and a textured region overlying a sealed chamber.

Optionally, a terminal area of the tongue portion 14 includes a sealed chamber 16. The sealed chamber contains air, a liquid, or as depicted in FIG. 3F, a self-contained miniature battery-powered flashlight or vibrator circuit.

The shield portion 12 is attached to a strap 18. The strap 18 is suited to encompass the back of a wearer head and tension the inventive bib 10 against a user face while the shield portion 12 surrounding a user chin prevents inadvertent bib dislocation during usage. It is appreciated that an inventive bib 10 including the strap 18 is readily formed from a unitary material. Alternatively, a strap 18 is formed of a different material or greater thickness of material relative to the shield portion. Conventional joiners for adhering a strap to a thin shield portion illustratively include contact adhesives, thermal welding, sonic welding, and stitches.

Figure 6:
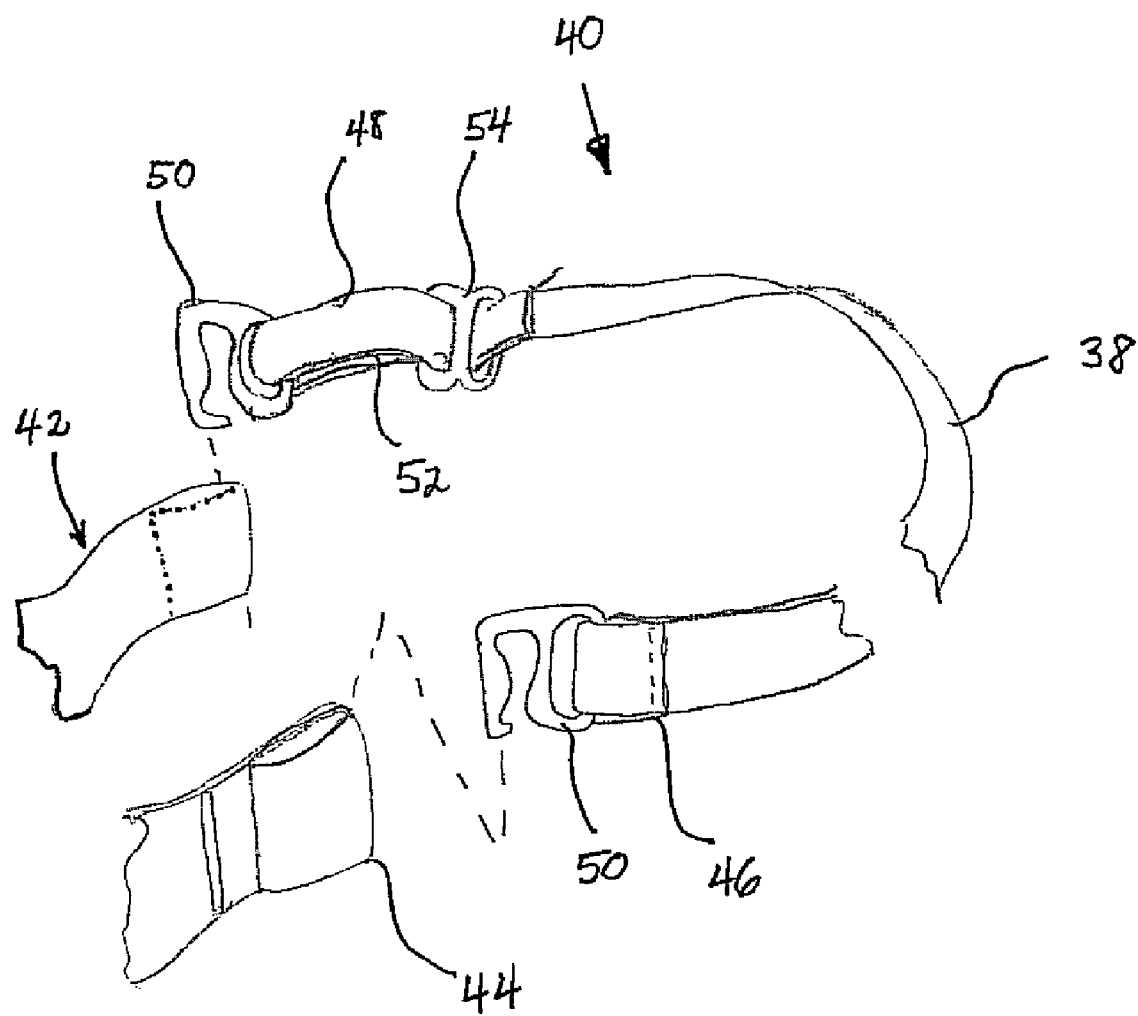
FIG. 6 is a partial cutaway exploded view of a separate ribbon strap-shield portion oral bib joining arrangement.

As shown in FIG. 6, a strap 38 is readily formed from a flattened ribbon of elastomeric material. It has been found that a single ribbon having a rectilinear cross-section upon tensioning against the back of the head of a user retains an inventive bib 40 in position to a greater extent than a comparable circular cross-section elastomeric strap or even a pair of such straps. Additionally, the rectilinear cross-section elastomeric strap 38 does not suffer from becoming entangled in the hair of a user. Preferably, the strap has a height of 0.2-0.6 inches.

In a preferred embodiment, a strap 38 formed of a separate material relative to the shield portion 42 is joined thereto by forming terminal loops 44 in the shield portion 42 by rolling the shield end onto itself and joining the overlapped material with an adhesive, sonic welding, or stitching. The shield portion 42 has all the attributes of shield portion 12 as detailed above with the exception of the loops 44 in place of a unitary construct with a strap 18. The shield portion 42 specifically is amenable to inclusion of the attributes detailed in the preceding figures with respect to reference numerals 14, 15, 16, 20 and 22. The ends 46 and 48 of the straps 38 are terminated with complementary hooks 50 relative to the shield portion loops 44. More preferably, one of the hooks 50 is held by a loop 52 of strap material simultaneously engaging a slide 54 so as to allow for strap adjustment.

Optionally, a hole 20 or cutout 22 is placed in the shield portion so as to overlie a wearer cheek and afford greater comfort without sacrificing the protective aspects of an inventive bib.

It is appreciated that an inventive bib is suitable for modification with conventional additives illustratively including pigments or dyes, antimicrobial compounds, fragrances, plasticizers and the like. Additionally, an inventive bib is amenable to dusting with conventional anti-stick powders such as talc, cornstarch and the like.

Figure 5:
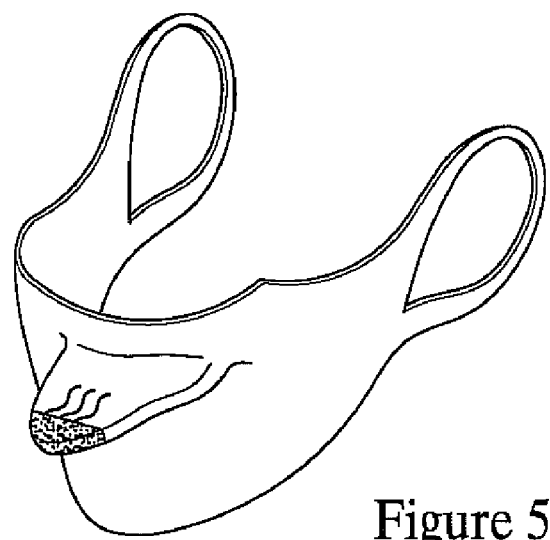
FIG. 5 is a perspective view of an inventive embodiment having ear loops.

FIGS. 4A-4F illustrate alternate strap configurations operative with an inventive bib. The strap configuration depicted in FIG. 5 is adapted to encompass the ears of a wearer such that contact with a user chin and the two ear straps forms a three-point retention system.

The present invention is amenable to various modifications by one of ordinary skill in the art to which the invention pertains. These modifications nonetheless retain the spirit of the present invention. These modifications and equivalents thereof are intended to be encompassed within the scope of the appended claims.

The invention claimed is:

1. An oral bib comprising: a thin sheet protective shield portion having resistance to passage of a sexually transmitted disease microbe therethrough formed of an elastomeric material, said shield portion configured to overlie a chin and mouth region of a wearer and having opposing sides ending in terminal loops, said shield portion configured to terminate intermediate between a wearer nose and the mouth region of the wearer; a tongue portion with a separate sealed chamber extending from the tip of said tongue portion, said tongue portion extending from said protective shield portion and overlying the wearer mouth region, said chamber includes therein an item selected from the group consisting of: air, a liquid, a flashlight circuit, and a vibrator circuit; and a single elastic ribbon strap adapted to secure said shield portion to a wearer head said strap forming a loop with said shield, the loop configured to encompass a wearer head, said strap terminating in hooks adapted to engage the terminal loops of said shield portion.

2. The bib of claim 1 wherein said protective shield portion is formed of a latex rubber.

3. The bib of claim 1 wherein said tongue portion and said protective shield portion are unitary.

4. The bib of claim 1 wherein said tongue portion is distinct from said protective shield portion with a hermetic seal therebetween.

5. The bib of claim 1 wherein said tongue portion has a contour thereon.

6. The bib of claim 5 wherein said contour is one selected from the group consisting of longitudinal waves, pilli, transverse waves, dimples, a step, and a raised textured region.

7. The bib of claim 1 wherein the shield portion has a cutout aperture therethrough.

8. An oral bib comprising: a thin sheet protective shield portion having resistance to passage of a sexually transmitted disease microbe therethrough formed of an elastomeric material, said shield portion configured to overlie a chin and mouth region of a wearer and having opposing sides a tongue portion with a separate sealed chamber extending from the tip of said tongue portion, said tongue portion extending from said protective shield portion and overlying the wearer mouth region, said chamber includes therein an item selected from the group consisting of: air, a liquid, a flashlight circuit, and a vibrator circuit; said shield configured to terminate intermediate between a wearer nose and the mouth region of the wearer and consisting of a single elastic ribbon strap adapted to secure said shield portion to a wearer head, said strap forming a loop with said shield, the loop configured to encompass a wearer head.

9. The bib of claim 8 wherein said tongue portion and said protective shield portion are unitary.

10. The bib of claim 8 further comprising a slide to provide a length adjustment to said strap.

11. The bib of claim 8 wherein said contour is one selected from the group consisting of longitudinal waves, pilli, transverse waves, dimples, a step, and a raised textured region.

* * * * *